US012599501B2

(12) United States Patent
Han

(10) Patent No.: US 12,599,501 B2
(45) Date of Patent: Apr. 14, 2026

(54) EYE DISEASE IMPLANT DEVICE CAPABLE OF LOWERING EYE PRESSURE BY EASY AND SAFE METHOD

(71) Applicant: MICROT INC., Seoul (KR)

(72) Inventor: Jong Chul Han, Seoul (KR)

(73) Assignee: MICROT INC., Seoul (KR)

( * ) Notice: Subject to any disclaimer, the term of this patent is extended or adjusted under 35 U.S.C. 154(b) by 943 days.

(21) Appl. No.: 17/777,303

(22) PCT Filed: Oct. 20, 2020

(86) PCT No.: PCT/KR2020/014288
§ 371 (c)(1),
(2) Date: May 17, 2022

(87) PCT Pub. No.: WO2021/101080
PCT Pub. Date: May 27, 2021

(65) Prior Publication Data
US 2022/0395396 A1     Dec. 15, 2022

(30) Foreign Application Priority Data

Nov. 19, 2019     (KR) ......................... 10-2019-0148783

(51) Int. Cl.
*A61F 9/007*          (2006.01)
*A61M 27/00*          (2006.01)
(52) U.S. Cl.
CPC ......... *A61F 9/00781* (2013.01); *A61M 27/00* (2013.01); *A61F 2250/0096* (2013.01)
(58) Field of Classification Search
CPC ........ A61F 9/00781; A61F 2009/00891; A61F 9/0017; A61F 9/007; A61F 2210/0014;
(Continued)

(56) References Cited

U.S. PATENT DOCUMENTS 4,554,918 A * 11/1985 White ................. A61F 9/00781
604/10
5,073,163 A * 12/1991 Lippman ............. A61F 9/00781
604/9
(Continued)

FOREIGN PATENT DOCUMENTS

JP         2012125606 A       7/2012
JP         2014500758 A       1/2014
(Continued)

OTHER PUBLICATIONS

PCT International Search Report and Written Opinion from PCT/KR2020/014288, mailed on Jan. 27, 2021, 14 pages.

*Primary Examiner* — Adam Marcetich
(74) *Attorney, Agent, or Firm* — ZION IP; Byungwoong Park

(57)          ABSTRACT

The present disclosure relates to an eye disease implant device, and an eye disease implant device according to an embodiment of the present disclosure includes a tube including a hollow portion through which aqueous humor is drained, wherein one or more wings extending in a direction different from a longitudinal direction of the tube are formed on a portion of an outer surface of the tube. Also, the eye disease implant device may further include a body including a receiving space into which an end of the tube is inserted. In this case, the end of the tube may be inserted into the receiving space to be coupled to the body, or detached from the receiving space to be separated from the body.

7 Claims, 8 Drawing Sheets

(58) Field of Classification Search
CPC ... A61F 2220/0016; A61M 2210/0612; A61M
27/00; A61M 27/002; A61M 2025/0004;
A61L 27/14; A61L 31/04
See application file for complete search history.

(56) References Cited

U.S. PATENT DOCUMENTS

| | | | | |
|---|---|---|---|---|
| 5,346,464 | A * | 9/1994 | Camras | A61F 9/00781 |
| | | | | 604/9 |
| 5,405,341 | A * | 4/1995 | Martin | A61M 25/0026 |
| | | | | 604/523 |
| 5,626,558 | A * | 5/1997 | Suson | A61F 9/00781 |
| | | | | 604/9 |
| 5,725,493 | A * | 3/1998 | Avery | A61F 9/0017 |
| | | | | 604/9 |
| 6,589,203 | B1 * | 7/2003 | Mitrev | A61M 27/002 |
| | | | | 604/9 |
| 9,381,112 | B1 * | 7/2016 | Sponsell | A61F 9/0017 |
| 9,421,130 | B2 | 8/2016 | Juan, Jr. | |
| 9,808,374 | B2 | 11/2017 | Chew et al. | |
| 10,772,762 | B2 | 9/2020 | Pinchuk | |
| 10,945,883 | B2 | 3/2021 | Kahook et al. | |
| 2002/0026200 | A1 * | 2/2002 | Savage | A61F 9/00781 |
| | | | | 606/108 |
| 2002/0193725 | A1 | 12/2002 | Odrich | |
| 2003/0236483 | A1 * | 12/2003 | Ren | A61F 9/00781 |
| | | | | 606/107 |
| 2004/0015140 | A1 | 1/2004 | Shields | |
| 2004/0024453 | A1 | 2/2004 | Castillejos | |
| 2004/0073156 | A1 * | 4/2004 | Brown | A61F 9/00781 |
| | | | | 604/8 |
| 2006/0189916 | A1 * | 8/2006 | Bas | A61F 9/00781 |
| | | | | 604/8 |
| 2006/0189917 | A1 * | 8/2006 | Mayr | A61F 9/00781 |
| | | | | 604/9 |
| 2007/0293807 | A1 | 12/2007 | Lynch et al. | |
| 2008/0125691 | A1 * | 5/2008 | Yaron | A61F 9/00781 |
| | | | | 604/9 |
| 2009/0182421 | A1 * | 7/2009 | Silvestrini | A61F 9/00781 |
| | | | | 623/6.14 |
| 2010/0004635 | A1 * | 1/2010 | Lin | A61F 9/00781 |
| | | | | 216/37 |
| 2013/0150773 | A1 * | 6/2013 | Nissan | A61F 9/00781 |
| | | | | 604/9 |
| 2015/0148729 | A1 * | 5/2015 | Pinchuk | A61M 27/002 |
| | | | | 604/8 |
| 2015/0173644 | A1 | 6/2015 | Ren et al. | |
| 2016/0058615 | A1 * | 3/2016 | Camras | A61F 9/00781 |
| | | | | 604/9 |
| 2017/0367888 | A1 * | 12/2017 | Brown | A61L 27/18 |
| 2019/0388273 | A1 * | 12/2019 | Ferentini | A61F 9/00781 |
| 2020/0129332 | A1 * | 4/2020 | Van Der Mooren | A61F 9/007 |
| 2020/0229977 | A1 * | 7/2020 | Mixter | A61F 9/0017 |
| 2021/0161713 | A1 * | 6/2021 | Bouremel | B29C 48/11 |

FOREIGN PATENT DOCUMENTS

| | | |
|---|---|---|
| JP | 2015506748 A | 3/2015 |
| JP | 2017506139 A | 3/2017 |
| JP | 2019517312 A | 6/2019 |
| KR | 20010032324 A | 4/2001 |
| KR | 20050016443 A | 2/2005 |
| KR | 20140120906 A | 10/2014 |
| KR | 20150034010 A | 4/2015 |
| KR | 200481784 Y1 | 11/2016 |
| KR | 20180098303 A | 9/2018 |
| WO | 2012068123 A1 | 5/2012 |
| WO | 2013147978 A2 | 10/2013 |
| WO | 2017210561 A2 | 12/2017 |
| WO | 2018232248 A1 | 12/2018 |

* cited by examiner

【FIG. 1】
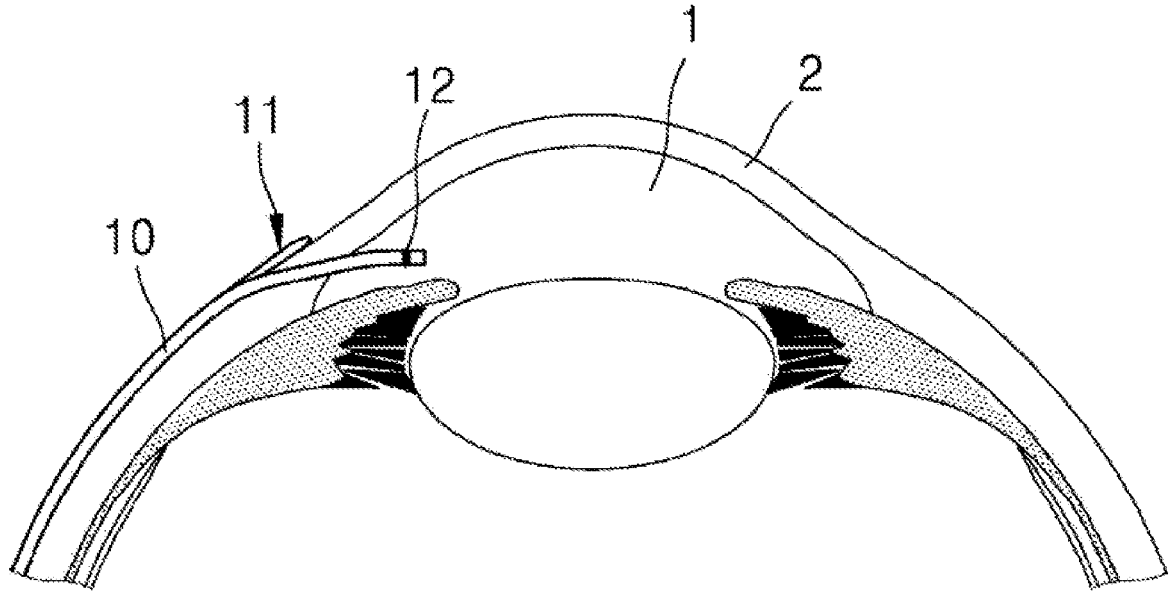
【FIG. 2】
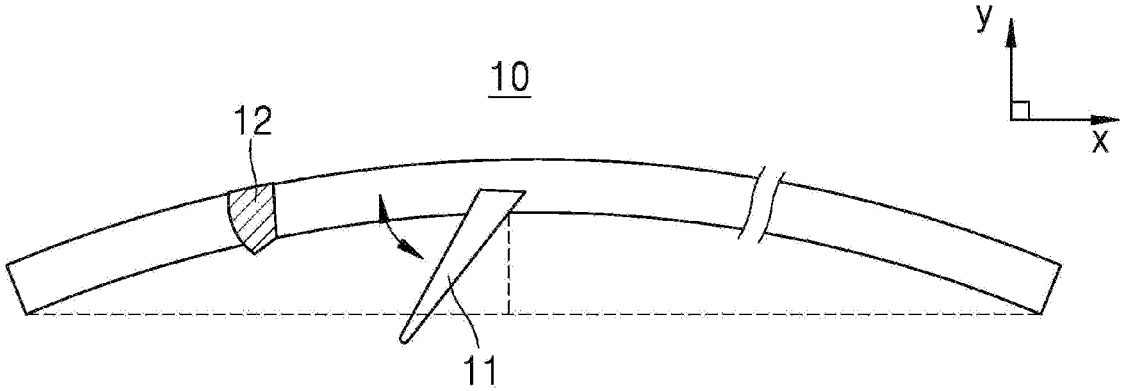

【FIG. 3】
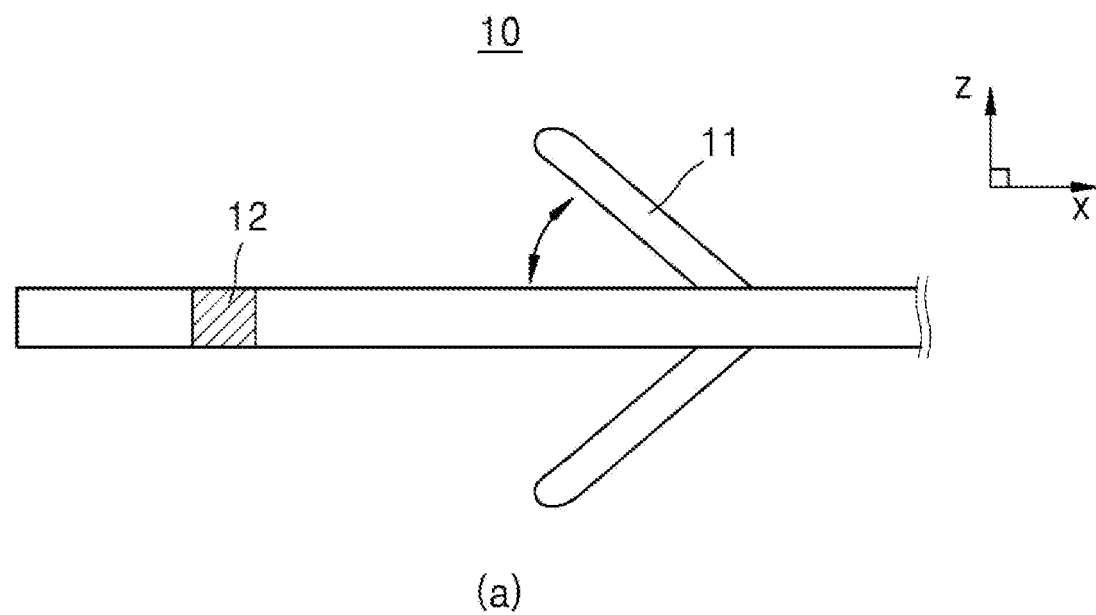
(a)
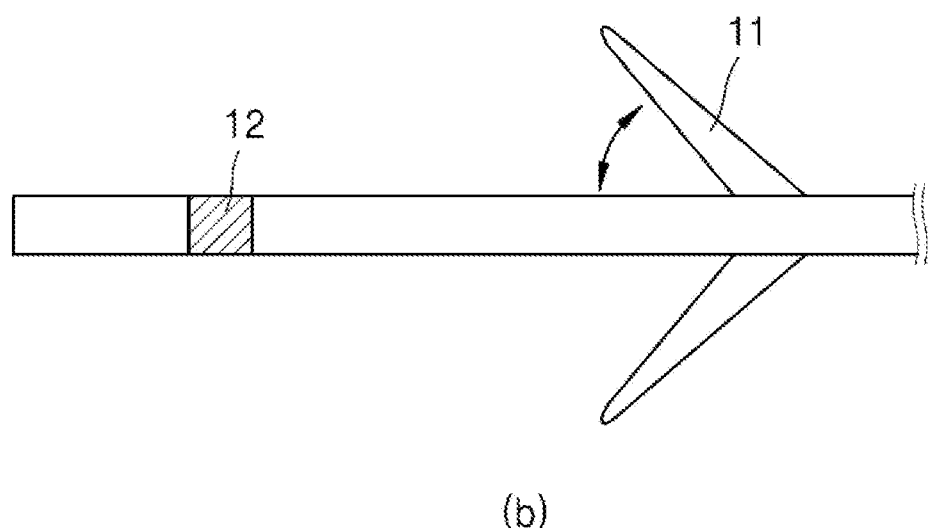
(b)

【FIG. 4】
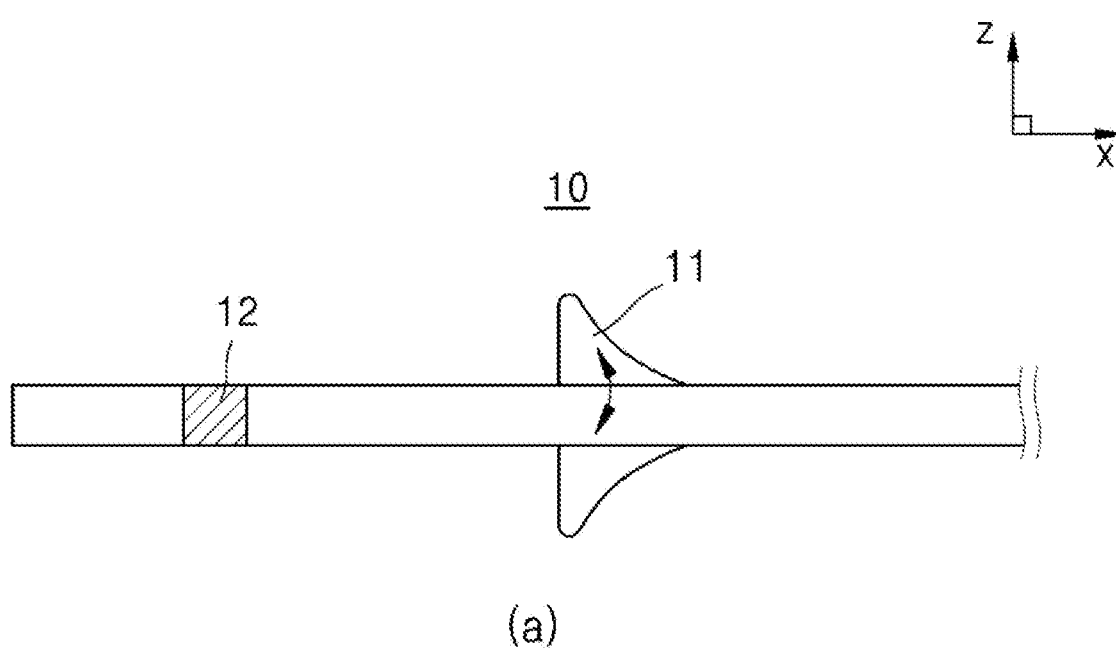
(a)
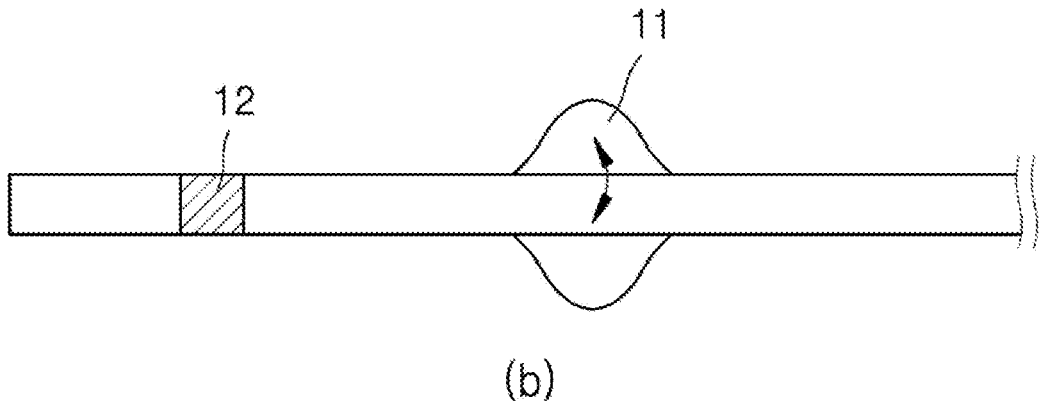
(b)

【FIG. 5】
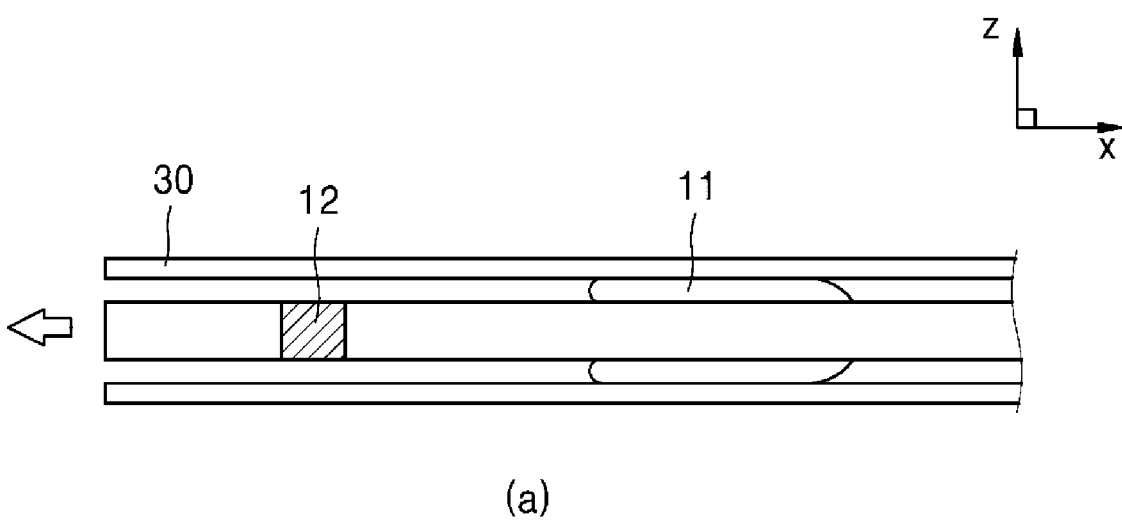
(a)
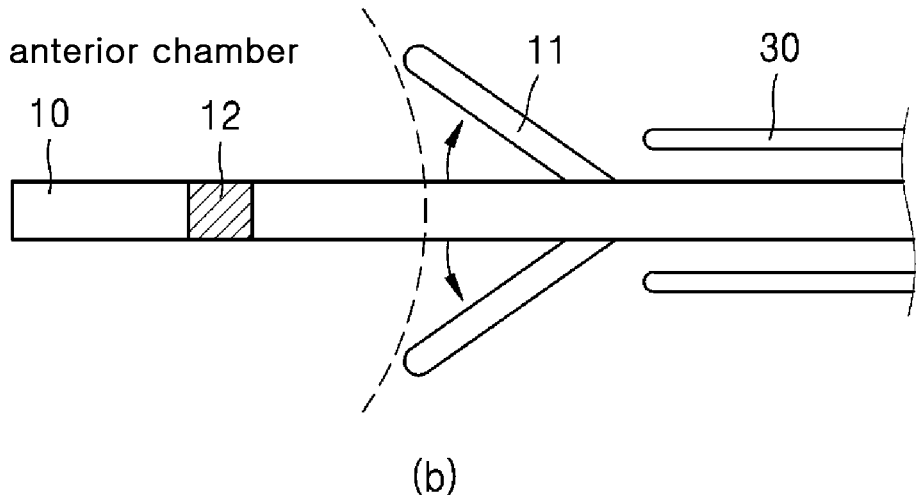
(b)

【FIG. 6A】
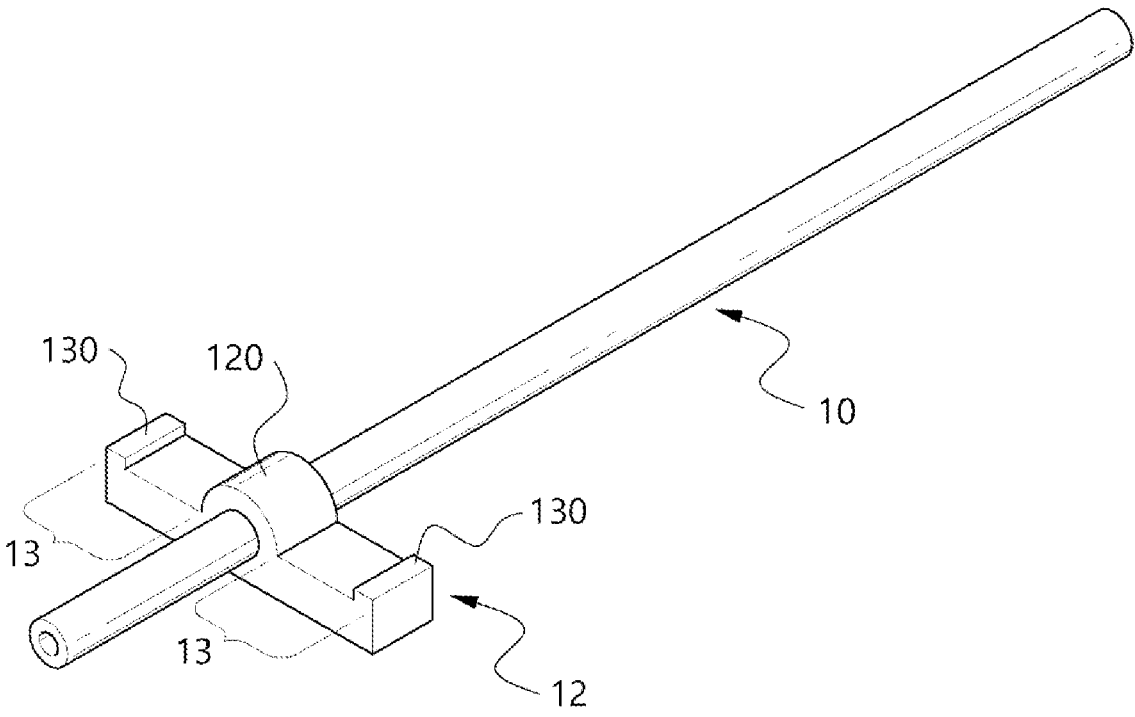
【FIG. 6B】
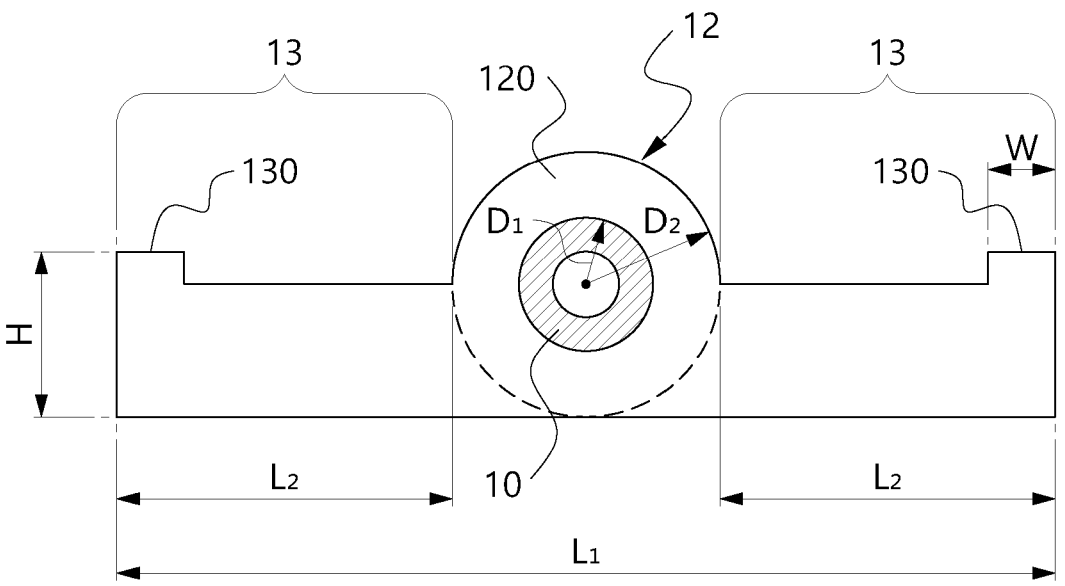

【FIG. 7A】
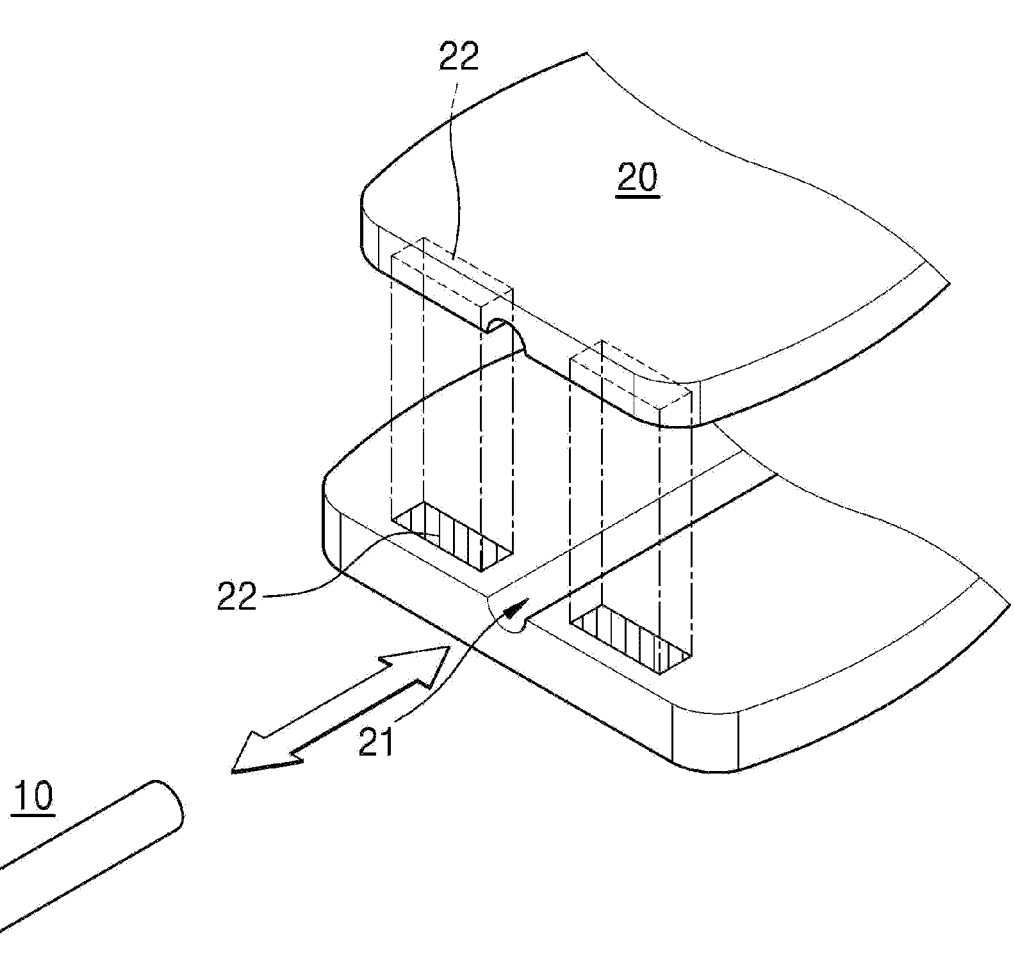

【FIG. 7B】
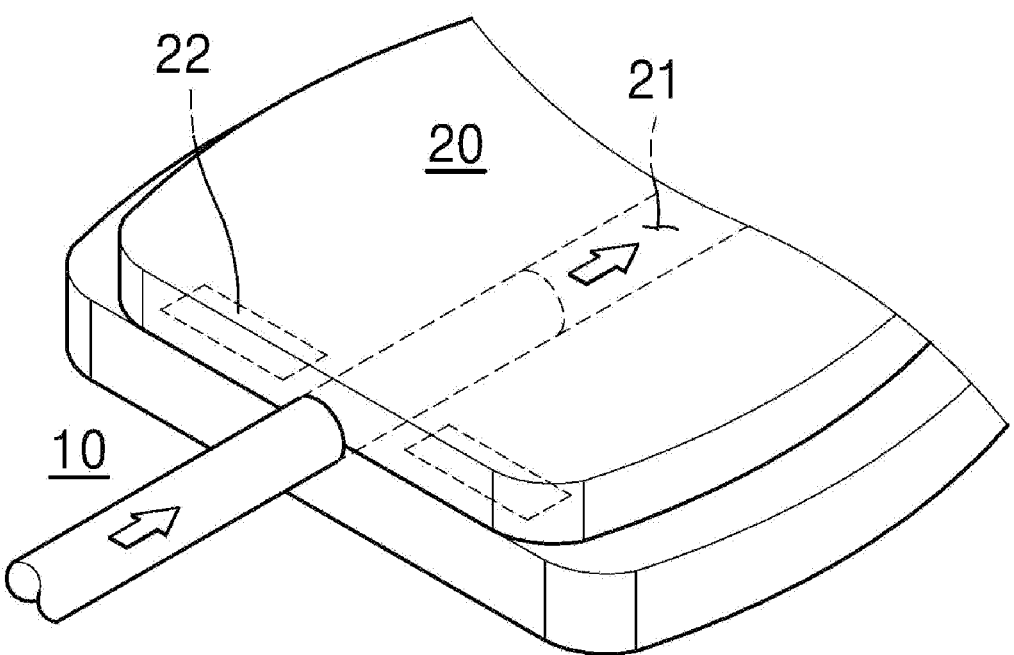

【FIG. 8】
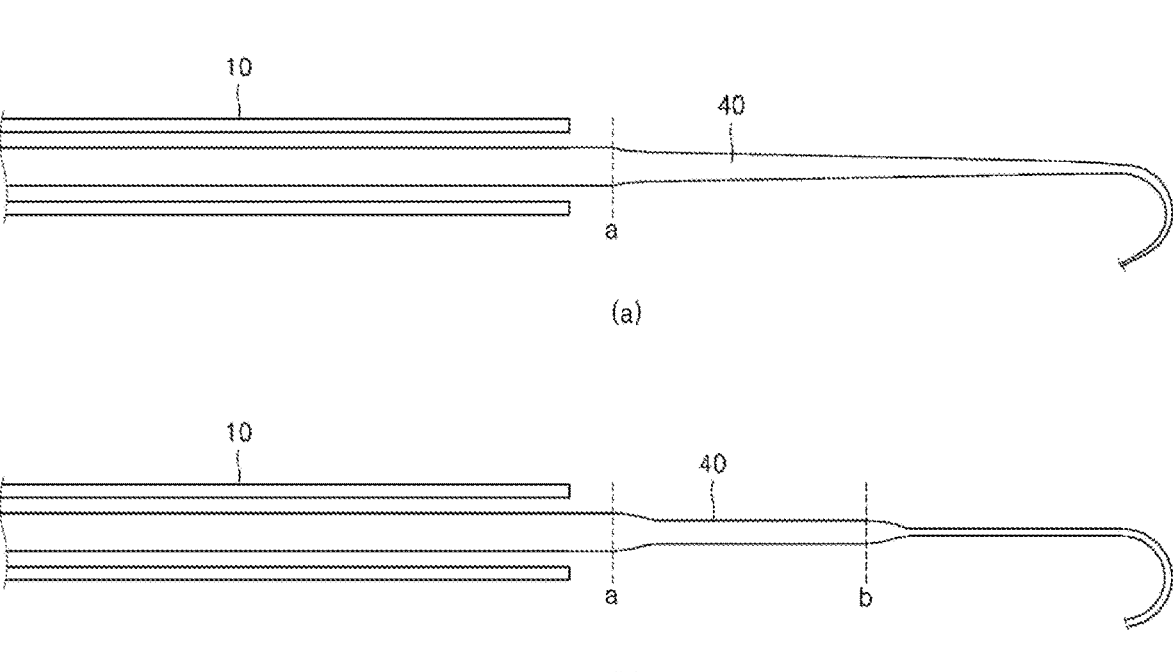
(a)
(b)

EYE DISEASE IMPLANT DEVICE CAPABLE OF LOWERING EYE PRESSURE BY EASY AND SAFE METHOD

CROSS-REFERENCE TO RELATED APPLICATIONS

This application is a national phase entry pursuant to 35 U.S.C. § 371 of International Application No. PCT/KR2020/014288, filed Oct. 20, 2020, which claims priority to Korean Application No. 10-2019-0148783, filed Nov. 19, 2019, the entire contents of each of which are incorporated by reference herein for all purposes.

TECHNICAL FIELD

The present disclosure relates to an eye disease implant device, and more particularly, to an eye disease implant device having a structure that may be easily and safely placed and fixed by a surgeon when being inserted into an eyeball and in which a tube and a body may be combined with or separated from each other according need or circumstances.

BACKGROUND ART

For a glaucoma patient whose intraocular pressure is not controlled even by using an intraocular pressure lowering agent, intraocular pressure is lowered by creating a bypass to drain aqueous humor from the anterior chamber of an eye to an external surface of the eye under the conjunctiva. Trabeculectomy among glaucoma filtration surgeries that create a bypass or a fistula for aqueous humor drainage may fail to control intraocular pressure when the amount of aqueous humor drainage decreases due to closure of the bypass after surgery. When initial surgery fails and glaucoma filtration surgery is performed again, the frequency of bypass closure after surgery increases and a success rate of surgery is low.

Also, even in the case of intractable glaucoma such as neovascular glaucoma or secondary glaucoma caused by uveitis according to types of glaucoma, closure of a bypass frequently occurs after trabeculectomy, resulting in poor results. For an eye with a history of failed glaucoma filtration surgery or intractable glaucoma, glaucoma implant surgery of locating a glaucoma implant device is performed to prevent closure of a bypass and increase a success rate of surgery. To date, glaucoma implant surgery has been used as an alternative to trabeculectomy, especially in several difficult-to-treat glaucoma, in that glaucoma implant surgery not only effectively lowers intraocular pressure but also shows a predictable postoperative clinical course according to an inner diameter of a given tube.

However, an existing glaucoma implant used for glaucoma implant surgery may cause various problems and complications such as difficulty in surgery due to a relatively large size, postoperative exposure, infection, eye movement disorder due to a large body, and diplopia. Accordingly, small-sized glaucoma implant instruments (microinvasive glaucoma surgery (MIGS)) have recently been developed to relatively easily lower intraocular pressure by using a glaucoma implant and to reduce side effects after surgery due to a large size.

Surgery using a small-sized glaucoma implant has an advantage in that surgery may be completed by simply inserting a small-sized glaucoma implant under the conjunctiva into the anterior chamber of an eyeball, but there is still much controversy over how the small-sized glaucoma implant may be inserted into the anterior chamber 1) easily and 2) safely. In general, glaucoma implant surgery of locating a glaucoma implant device may be divided into a method in which after exfoliating conjunctival tissue or Tenon tissue of an eyeball, a surgeon directly inserts a tube into the anterior chamber, and an injection method using an injector.

The method in which the surgeon directly inserts the tube into the anterior chamber may allow the surgeon to place the glaucoma implant device at a position inside the eyeball for aqueous humor drainage while watching, but has a disadvantage in that damage may occur in a process of directly placing the glaucoma implant and a considerable skill is required of the surgeon. In contrast, the injection method using the injector may insert the implant into the anterior chamber regardless of the surgeon's experience, but even in this case, has a disadvantage in that it is difficult to stably place and fix the glaucoma implant device at an exact position for aqueous humor drainage.

DISCLOSURE

Technical Problem

According to an aspect of the present disclosure, the present disclosure aims to provide an eye disease implant device structured so that a clinician performing surgery can accurately determine a position of a tube in a process of placing or injecting the tube into an eyeball and the tube can be stably fixed at an exact position.

In addition, the present disclosure also aims to provide an eye disease implant device having a structure for minimizing eyeball damage and complications caused by a tube placed or injected into an eyeball and for allowing the tube and a body to be combined with or separated from each other according to need or circumstances.

Technical Solution

An eye disease implant device according to an embodiment of the present disclosure includes a tube including a hollow portion through which aqueous humor is drained, wherein one or more wings extending in a direction different from a longitudinal direction of the tube are formed on a portion of an outer surface of the tube.

The one or more wings may be foldably provided, and may be unfolded while the tube is inserted into an anterior chamber of an eyeball by an injector to prevent the tube from being inserted beyond a certain point and fix a position of the tube.

Each of the one or more wings may have one of a straight bar shape, a tapered bar shape, a triangular shape, and a semicircular shape.

A marker with a color for checking a position of the tube in an eyeball may protrude from a portion of the outer surface of the tube.

The tube may be formed in a curved shape with a certain curvature to prevent damage to corneal endothelium in an eyeball due to the tube.

The eye disease implant device may further include a support having a fixing hole into which the tube is inserted, and extending in a direction different from the longitudinal direction of the tube to form the one or more wings.

The eye disease implant device may further include a body including a receiving space into which an end of the tube is inserted. The end of the tube may be inserted into the receiving space to be coupled to the body, or detached from the receiving space to be separated from the body.

The eye disease implant device may further include a wick insertable into the hollow portion of the tube to control an amount of aqueous humor drainage.

A diameter of the wick may change from a certain point.

Advantageous Effects

According to an eye disease implant device provided as an embodiment of the present disclosure, because a tube may be placed at an exact position and may be stably fixed while being placed or injected into an eyeball through a marker and a wing formed in the tube, the surgical convenience of a clinician and the surgical stability of a patient may be reliably ensured.

Also, contrary to the prior art, side effects such as damage to corneal endothelium and corneal decompensation due to the tube placed and injected into an eyeball may be minimized by using a tube manufactured to be manufactured in a curved shape along a curvature of an eye surface.

In addition, because a tube and a body are selectively combined with or separated from each other, optimal surgery may be performed in consideration of a clinical situation, a patient's condition, etc. That is, compared to the prior art, surgical conditions and environments for effective aqueous humor drainage and treatment of eye diseases may be provided.

DESCRIPTION OF DRAWINGS

FIG. 1 is a view illustrating a state where an eye disease implant device is inserted into an eyeball according to an embodiment of the present disclosure.

FIG. 2 is a side view illustrating a tube according to an embodiment of the present disclosure.

FIGS. 3 and 4 are plan views illustrating a tube according to an embodiment of the present disclosure.

FIG. 5 is a view illustrating a process of inserting a tube into an eyeball through an injector according to an embodiment of the present disclosure.

FIG. 6A is a perspective view illustrating a tube according to another embodiment of the present disclosure.

FIG. 6B is a cross-sectional view illustrating the tube of FIG. 6A.

FIG. 7A is a conceptual view illustrating a coupling process between a tube and a body according to an embodiment of the present disclosure.

FIG. 7B is a perspective view illustrating a state where a tube and a body are coupled to each other according to an embodiment of the present disclosure.

FIG. 8 is a plan view illustrating a wick inserted into a tube according to an embodiment of the present disclosure.

BEST MODE

The terms used herein will be briefly described, and the present disclosure will be described in detail.

The terms used herein are those general terms currently widely used in the art in consideration of functions in the present disclosure but the terms may vary according to the intention of one of ordinary skill in the art, precedents, or new technology in the art. Also, some of the terms used herein may be arbitrarily chosen by the present applicant, and in this case, these terms are defined in detail below. Accordingly, the specific terms used herein should be defined based on the unique meanings thereof and the whole context of the present disclosure.

It will be understood that when a certain part "includes" a certain component, the part does not exclude another component but may further include another component, unless the context clearly dictates otherwise. Also, throughout the specification, when an element is referred to as being "connected" to another element, it will be understood to include that the element is "directly connected" to the other element or is "connected" to the other element with another element therebetween.

Hereinafter, embodiments of the present disclosure will be described in detail with reference to the accompanying drawings so that the embodiments of the present disclosure may be easily implemented by one of ordinary skill in the art. However, the present disclosure may be embodied in many different forms and is not limited to the embodiments of the present disclosure set forth herein. For clarity, portions irrelevant to the descriptions of the present disclosure are omitted in the drawings, and like components are denoted by like reference numerals throughout the specification.

Hereinafter, the present disclosure will be described in detail with reference to the accompanying drawings.

FIG. 1 is a view illustrating a state where an eye disease implant device is inserted into an eyeball according to an embodiment of the present disclosure.

An eye disease implant device according to an embodiment of the present disclosure may be injected into an eyeball through an injector in a manner that a part of the eye disease implant device is inserted into an anterior chamber 1 of the eyeball formed by a cornea 2 as shown in FIG. 1. The injector refers to a device for pushing an implant device accommodable herein with a mechanical force and injecting the implant device into the eyeball. In addition to a method using the injector, the implant device may be located in a manner that a portion of which is directly inserted by a surgeon into the anterior chamber 1 through exfoliated conjunctival tissue or Tenon tissue of the eyeball.

Referring to FIG. 1, a part of a front end of a tube 10 included in the implant device according to an embodiment of the present disclosure may be placed in the anterior chamber 1 of the eyeball, and the remaining part of the tube 10 may be located on the conjunctival tissue or Tenon tissue of the eyeball. That is, once the implant device is inserted, aqueous humor generated in the anterior chamber 1 of the eyeball flows along a hollow portion formed in the tube 10 to be drained to the conjunctival tissue or Tenon tissue, thereby controlling intraocular pressure.

The tube 10 may be formed of a biocompatible material, and/or a changeable material. In an embodiment, the tube 10 may be formed of, but not limited to, a urethane-based material such as polytetrafluoroethylene (PTFE) or polycarbonate polyurethane, a silicone-based material such as polydimethylsiloxane (PDMS), or a siloxane/polyurethane compound (siloxane-based polyurethane).

In this case, although not shown, a body 20 in which aqueous humor is temporarily accommodated to effectively control intraocular pressure may be provided at the rear of the tube 10. For example, after a part of the tube 10 is inserted into the anterior chamber 1 of the eyeball, the body 20 may be coupled and located at the rear of the tube 10 through the exfoliated conjunctival tissue or Tenon tissue in consideration of a clinical situation such as a rate of fibrosis or a change in a patient's condition. Alternatively, in a state where the tube 10 and the body 20 are initially coupled to each other (i.e., the tube 10 and the body 20 are integrally formed with each other), the tube 10 and the body 20 may be placed together inside the eyeball through the exfoliated conjunctival tissue or Tenon tissue of the eyeball. That is, the tube 10 may be previously coupled to the body 20 before the implant device is placed in the eyeball, or the tube 10 may be first placed in the eyeball and then may be coupled to the body 20 according to clinical need or circumstances. A structure, a shape, and a coupling relationship of the tube 10 and the body 20 included in the implant device will be described in more detail with reference to FIGS. 2 through 7.

According to an embodiment of the present disclosure, eye diseases may include glaucoma caused by an increase in intraocular pressure. Examples of glaucoma may include congenital glaucoma, traumatic glaucoma, glaucoma suspect, ocular hypertension, primary open-angle glaucoma, normal-tension glaucoma, capsular glaucoma with pseudo-exfoliation of lens, chronic simple glaucoma, low-tension glaucoma, pigmentary glaucoma, primary angle-closure glaucoma, acute angle-closure glaucoma, chronic angle-closure glaucoma, intermittent angle-closure glaucoma, glaucoma secondary to eye trauma, glaucoma secondary to eye inflammation, glaucoma secondary to drugs, neovascular glaucoma, and secondary glaucoma due to uveitis.

FIG. 2 is a side view illustrating the tube 10 according to an embodiment of the present disclosure. FIGS. 3 and 4 are plan views illustrating the tube 10 according to an embodiment of the present disclosure.

Referring to FIG. 2, the eye disease implant device according to an embodiment of the present disclosure includes the tube 10 having a hollow portion through which aqueous humor is drained. One or more wings 11 extending in a direction different from a longitudinal direction of the tube 10 may be formed on a portion of an outer surface of the tube 10. Also, the wing 11 may be attached to a portion of a surface of the tube 10, or the wing 11 and the tube 10 may be integrally formed by using the same material. Because a part of the tube 10 should be located in the anterior chamber 1 of the eyeball and the remaining part should be located on conjunctival tissue or Tenon tissue to drain aqueous humor as described above, the entire tube 10 should not be completely inserted into the anterior chamber 1 of the eyeball. That is, the wing 11 of the tube 10 prevents the tube 10 from being completely inserted into the anterior chamber 1 of the eyeball and stably fixes the tube 10 at an exact position.

In an embodiment, the wing 11 may be foldably provided, and may be folded or unfolded in the longitudinal direction of the tube 10 or a horizontal direction. For example, when the wings 11 are formed on both sides of the tube 10 as shown in FIG. 2, in a state where the wings 11 are completely unfolded, it is not easy to inject the tube 10 due to an overall volume and size. Also, in order for the tube 10 to be embedded in an injector 30, a diameter of the tube 10 may be limited within a certain range. Accordingly, in order for the tube 10 to be embedded in the injector 30 and to be injected into the eyeball, the wing 11 may be folded to be closely attached to the tube 10. The wing 11 folded to be closely attached to the tube 10 may be slowly unfolded while the tube 10 is injected, and after the tube 10 is sufficiently inserted into the anterior chamber 1 of the eyeball, the wing 11 may be completely unfolded to fix the tube 10. That is, the wing 11 may be maintained in a folded state to be closely attached to the tube 10 while the tube 10 is embedded in the injector 30, and then may be naturally unfolded while the tube 10 is injected into the anterior chamber 1 of the eyeball by the injector 30, thereby preventing additional insertion of the tube 10 into the anterior chamber 1 of the eyeball.

Referring to FIG. 2, a marker 12 with a color for checking a position of the tube 10 in the eyeball may protrude from a portion of the outer surface of the tube 10 according to an embodiment of the present disclosure. That is, in order for a clinician to easily check whether the tube 10 is sufficiently inserted to effectively drain aqueous humor in a surgical process of inserting the tube 10 into the anterior chamber 1 of the eyeball, the mark 12 may be formed at the front portion of the tube 10. In this case, the marker 12 may protrude to fix the tube 10 so that the tube 10 is not separated backward (i.e., to the conjunctival tissue or Tenon tissue). For example, the marker 12 may surround a portion of the outer surface of the tube 10 and a part of the marker 12 may protrude in a triangular shape. Because the part protruding in the triangular shape forms a stepped portion on the tube 10, the movement of the tube 10 in a front-back direction after the tube 101 is inserted may be minimized. The color of the marker 12 may be a fluorescent color or the like for easy recognition.

Referring to FIG. 2, the tube 10 according to an embodiment of the present disclosure may be formed in a curved shape with a certain curvature to prevent damage to the endothelium of the cornea 2 in the eyeball due to the tube 10. A front end of the tube 10 may poke and damage the cornea 2 in the anterior chamber 1 of the eyeball in a process of inserting the tube 10 into the anterior chamber 1 of the eyeball according to a size of the eyeball that is different for each patient, a skill level in injection of the tube 10, etc. Damage to the cornea 2 may cause complications such as corneal decompensation which require even future corneal transplantation. Accordingly, in order for the tube 10 to naturally move in a curved shape while being inserted into the anterior chamber 1 of the eyeball, the tube 10 may be manufactured in a curved shape with a certain curvature (i.e., a curvature of a surface of the eyeball) as shown in FIG. 2.

A length of the tube 10 according to an embodiment of the present disclosure may range from about 5 mm to about 10 mm, and may be determined according to a clinical status and may be used for surgery. Also, an inner diameter of the tube 10 may range from about 60 μm to about 250 μm, and an outer diameter of the tube 10 may range from about 150 μm to about 450 μm, and may be determined according to a clinical status and may be used for surgery.

Referring to FIGS. 3 and 4, the wing 11 according to an embodiment of the present disclosure may be manufactured in various shapes that may be folded or unfolded to obstruct an insertion direction of the tube 10. For example, the wing 11 may have a straight bar shape as shown in (A) of FIG. 2, or may have a tapered bar shape as shown in (B) of FIG. 2. In this case, in order to minimize damage to the inside of the eyeball while the wing 11 is unfolded, the wing 11 may be manufactured so that an end portion of the wing 11 has a smoothly curved corner. As such, when the wing 11 has a straight bar shape or a tapered bar shape, the wing 11 may be folded or unfolded with respect to a longitudinal central axis of the tube 10 as shown in FIG. 2. Also, the wing 11 may have a triangular shape as shown in (A) of FIG. 3 or may have a semicircular shape as shown in (B) of FIG. 3. As such, when the wing 11 has a triangular shape or a semicircular shape, the wing 11 may be folded or unfolded with respect to a horizontal central axis of the tube 10 as shown in FIG. 3. FIGS. 3 and 4 are merely examples related to a shape of the wing 11, and modifications may be made into various shapes for stably fixing the tube 10 as described above.

FIG. 5 is a view illustrating a process of inserting the tube 10 into an eyeball through an injector 30 according to an embodiment of the present disclosure.

Before the tube 10 is injected into the eyeball through the injector 30, the tube 10 may be stored inside the injector 30 as shown in (A) of FIG. 5. In this case, the wing 11 having a straight bar shape may be maintained in a folded state to be closely attached to an outer surface of the tube 10. That is, due to a limited diameter inside the injector 30, the wing 11 may be stored in a folded state with respect to a longitudinal central axis of the tube 10.

When the tube 10 is injected into the eyeball by a clinician's injector manipulation, the tube 10 may come out of the injector 30 through a front end of the injector 30. In this case, the wing 11 having the straight bar shape folded by an inner wall of the injector 30 may be gradually unfolded along a surface around an implant insertion portion (e.g., around a corneal limbus or the like) as shown in (B) of FIG. 5. When the wing 11 is completely unfolded, the tube 10 may no longer be inserted into the anterior chamber 1 of the eyeball due to an opposing force applied between the wing 11 and the anterior chamber 1 of the eyeball, and may be fixed at a current position. Accordingly, a position of the wing 11 formed on the tube 10 may be determined in consideration of a degree of insertion of the tube 10 for effectively draining aqueous humor. That is, because the wing 11 according to an embodiment of the present disclosure is unfolded when the tube 10 is inserted into the anterior chamber 1 of the eyeball by the injector 30, the tube 10 may be prevented from being inserted beyond a certain point and a position of the tube 10 may be fixed.

FIG. 6A is a perspective view illustrating a tube according to another embodiment of the present disclosure. FIG. 6B is a cross-sectional view illustrating the tube of FIG. 6A.

Referring to FIGS. 6A and 6B, the tube 10 of the present embodiment is coupled to a support 12 extending in a direction different from a longitudinal direction of the tube 10. For example, the tube 10 may be coupled to the support 12 by passing through a fixing hole formed in a central portion 120 of the support 12 having a circular cross-section. The support 12 extends in a direction different from the longitudinal direction of the tube 10 to intersect the tube 10, and a part of the support 12 extending outward from an outer surface of the tube 10 corresponds to a wing 13. Like the wing 11 described with reference to FIGS. 2 through 5, the wing 13 according to the present embodiment prevents the tube 10 from being completely inserted into an anterior chamber of an eyeball and stably fixes the tube 10 at an exact position.

Like in the embodiment described with reference to FIG. 2, a maker (not shown) for easily checking whether the tube 10 is sufficiently inserted into the eyeball may also be formed on the tube 10 according to an embodiment of FIGS. 6A and 6B. Also, the tube 10 according to the present embodiment may have a curved shape with a certain curvature to prevent damage to corneal endothelium in the eyeball.

In an embodiment, a protrusion 130 is formed on a portion of the wing 13. The protrusion is a portion protruding compared to other portions of the wing 13, that is, a portion having a width greater than that of the other portions of the support 12. For example, the protrusion 130 may be formed on a terminal end of each of the wings 13 on both ends of the tube 10. When the wing 13 is additionally fixed with a thread according to an embodiment if necessary, the protrusion functions as an uneven portion for preventing the fixing thread from slipping.

In an embodiment, an outer diameter $D_1$ of the tube 10 (i.e., a diameter of the fixing hole of the support 12) is about 0.2 mm, and an outer diameter $D_2$ of the central portion 120 of the support 12 in which the fixing hole is formed is about 0.4 mm. Also, in an embodiment, a length $L_1$ of the support 12 is about 1.4 mm, a height H of the support 12 including a height of the protrusion 130 is about 0.25 mm, and a width W of the protrusion 130 is about 0.1 mm. A length $L_2$ of each of the wings 13 formed on both ends of the central portion 120 of the support 12 is 0.5 mm.

However, these numerical values are merely examples, and dimensions of portions of the tube 10 and the support 12 may vary according to embodiments and are not limited to the numerical values described in the specification.

According to the present embodiment, without needing to attach or fix a member for forming a wing on the outer surface of the tube 10, the wing 13 may be easily formed by fixing the tube 10 to the support 12 that intersects the tube 10. The tube 10 on which the wing 13 is formed may be located so that a part is inserted into the anterior chamber 1 in a manner that a surgeon exfoliates conjunctival tissue or Tenon tissue of the eyeball and then inserts the tube 10 through the exfoliated conjunctival tissue or Tenon tissue of the eyeball.

However, the tube 10 according to the present embodiment may be inserted into the eyeball through an injector 30 as described with reference to FIG. 5, and in this case, the support 12 may be formed of a flexible material that may be inserted into the injector 30 when applying pressure to deform the support 12. For example, the support 12 may be pressed or rolled to be closely attached to the tube 10 and may be pushed into the injector 30. When the tube 10 is injected into the eyeball by a clinician's injector manipulation, the tube 10 and the support 12 may come out of the injector 30 through a front end of the injector 30, and the support 12 may be unfolded to function as the wing 13.

FIG. 7A is a conceptual view illustrating a coupling process between the tube 10 and the body 20 according to an embodiment of the present disclosure. FIG. 7B is a perspective view illustrating a state where the tube 10 and the body 20 are coupled to each other according to an embodiment of the present disclosure.

The implant device according to an embodiment of the present disclosure may further include the body 20 including a receiving space 21 into which an end of the tube 10 is inserted. The body 20 is a structure for preventing exposure and separation of the tube 10, temporarily accommodating aqueous humor, and preventing body tissue from closing a rear end of the tube in a long term. Because the body 20 is coupled to a rear portion of the tube 10, the body tissue may be prevented from closing the rear end of the tube 10 as time passes, thereby minimizing side effects of increasing intraocular pressure again. For example, the body 20 may have a rectangular shape having a diameter ranging from about 1 mm to about 3 mm, but a size or a shape of the body 20 may be modified in various ways according to a clinical situation.

For example, referring to FIGS. 7A and 7B, the body 20 may be divided into an upper body and a lower body. The canal-type receiving space 21 into which a rear portion of the tube 10 is inserted may be provided in the upper body and the rear body. Because the upper body and the lower body may be coupled to or separated from each other, the tube 10 and the body 20 may be easily coupled to or separated from each other through the coupling of the upper body and the lower body. In this case, an adhesive member or a fastening member 22 for coupling or separating the upper body and the lower body may be provided. The adhesive member may be formed of a water-soluble material whose adhesive force is generated and increased when contacting water, and may increase a coupling force between the upper body and the lower body due to aqueous humor transmitted from the tube 10. Also, the fastening member may be formed to have a physical structure for generating a coupling force through contact such as an uneven structure (⌐⌐⌐⌐). Also, when necessary, for ease of surgery, only the upper body may be used, without the lower body, to cover an end portion of the tube close to the sclera. In this case, the upper body is fixed to the sclera by using a medical adhesive or a suture.

Also, in an embodiment, a wing extending in a direction different from a longitudinal direction of the tube 10 may be formed by using the body 20 into which an end of the tube 10 is inserted. That is, when the body 20 itself extends to intersect the tube 10 like the support 12 of FIGS. 6A and 6B, the body 20 coupled to the tube 10 may function as a wing for preventing the tube 10 from being completely inserted into an anterior chamber of an eyeball and fixing the tube 10 at an exact position.

FIG. 8 is a plan view illustrating a wick 40 inserted into the tube 10 according to an embodiment of the present disclosure.

Referring to FIG. 8, the implant device according to an embodiment of the present disclosure may further include the wick 40 that may be inserted into a hollow portion of the tube 10 to control the amount of aqueous humor drainage. The wick 40 that is inserted into the implant device so that a clinician easily controls intraocular pressure of the implant device may be a non-absorbable surgical suture thread, and may be formed of a nylon or prolene material. For example, when the wick 40 is inserted into the hollow portion of the tube 10 and exposed from a rear end of the tube 10, the clinician may control the amount of aqueous humor drainage by adjusting the wick 40 exposed from the rear end of the tube 10. That is, the clinician may appropriately control intraocular pressure according to a patient's condition by using the wick 40.

The wick 40 according to an embodiment of the present disclosure may have a diameter that may change from a certain point. The wick 40 may pass through the tube 10 and the body 20 and may be exposed out of an eyeball to facilitate control and removal by the clinician. In this case, when a wick having a constant diameter is used, a patient may have a severe foreign body sensation due to the wick passing through the inside of the eyeball and exposed to the outside. In order to solve this problem, the wick 40 may be manufactured to have a diameter that gradually decreases from a point at which the wick 20 is exposed from the tube 10 or the body 20. For example, a diameter of the wick 40 inserted into the hollow portion of the tube 10 may have a constant size, whereas a diameter of the wick 40 may gradually decrease from a point a from which the wick 40 passes through the rear end of the tube 10 and is exposed as shown in (A) of FIG. 8. Also, the wick 40 may be manufactured to have a diameter that decreases once at the point a from which the wick 40 passes through the rear end of the tube 10 and is exposed, is maintained, and decreases again at a point b as shown in (B) of FIG. 8. That is, the wick 40 may be manufactured to have a diameter that gradually decreases from a certain point.

The above description of the present disclosure is provided for illustration, and it will be understood by one of ordinary skill in the art that various changes in form and details may be readily made therein without departing from essential features and the scope of the present disclosure as defined by the following claims. Hence, it will be understood that the embodiments of the present disclosure should be considered in descriptive sense only and not for purposes of limitation. For example, each component described as a single type may be executed in a distributed manner, and components described as a distributed type may be executed in a combined manner.

The scope of the present disclosure is indicated by the claims rather than by the detailed description of the present disclosure, and it should be understood that the claims and all modifications or modified forms drawn from the concept and scope of the claims and equivalents are included in the scope of the present disclosure.

INDUSTRIAL APPLICABILITY

The present disclosure relates to an eye disease implant device, and more particularly, to an eye disease implant device having a structure that may be easily and safely placed and fixed by a surgeon when being inserted into an eyeball and in which a tube and a body may be combined with or separated from each other according need or circumstances.

The invention claimed is:

1. An eye disease implant device comprising a tube comprising a hollow portion through which aqueous humor is drained,
   wherein
   one or more wings extending in a direction different from a longitudinal direction of the tube are formed on a portion of an outer surface of the tube,
   the one or more wings are formed by a support comprising a fixing hole into which the tube is inserted, and the support extends in a direction different from the longitudinal direction of the tube,
   the support is located at a position of the tube with a predetermined distance from one of terminal ends of the tube, such that both the terminal ends of the tube are exposed,
   a protrusion is formed on each of terminal ends of the support,
   the protrusion has a width greater than a width of the other portions of the support, such that the protrusion functions as an uneven portion for preventing a fixing thread from slipping, and
   the protrusion is formed in an orthogonal direction to the longitudinal direction of the tube and an extending direction of the one or more wings.

2. The eye disease implant device according to claim 1, wherein the one or more wings are foldably provided, and are unfolded while the tube is inserted into an anterior chamber of an eyeball by an injector to prevent the tube from being inserted beyond a certain point and fix a position of the tube.

3. The eye disease implant device according to claim 2, wherein each of the one or more wings has one of a straight bar shape, a tapered bar shape, a triangular shape, and a semicircular shape.

4. The eye disease implant device according to claim 1, wherein a marker with a color for checking a position of the tube in an eyeball protrudes from a portion of the outer surface of the tube.

5. The eye disease implant device according to claim 1, wherein the tube is formed in a curved shape with a certain curvature to prevent damage to corneal endothelium in an eyeball due to the tube.

6. The eye disease implant device according to claim 1, further comprising a wick insertable into the hollow portion of the tube to control an amount of aqueous humor drainage.

7. The eye disease implant device according to claim 6, wherein a diameter of the wick changes from a certain point.

* * * * *